US012616440B2

(12) United States Patent　　　　(10) Patent No.:　US 12,616,440 B2

Neumann et al.　　　　　　　　　　(45) Date of Patent:　May 5, 2026

(54) ROBUST VIEW CLASSIFICATION AND MEASUREMENT IN ULTRASOUND IMAGING

(71) Applicant: Siemens Medical Solutions USA, Inc., Malvern, PA (US)

(72) Inventors: Dominik Neumann, Erlangen (DE); Awais Mansoor, Potomac, MD (US); Vlad Comanelea-Serban, Brasov (RO); Sasa Grbic, Plainsboro, NJ (US); Mallory Selzo, Kirkland, WA (US); Andrzej Milkowski, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1 day.

(21) Appl. No.: 18/969,359

(22) Filed: Dec. 5, 2024

(65) Prior Publication Data

US 2025/0094539 A1　　Mar. 20, 2025

Related U.S. Application Data

(63) Continuation of application No. 17/325,257, filed on May 20, 2021, now Pat. No. 12,197,542.

(51) Int. Cl.
| | |
|---|---|
| *A61B 8/08* | (2006.01) |
| *A61B 8/00* | (2006.01) |
| *G06V 20/70* | (2022.01) |

(52) U.S. Cl.
　　CPC .............. *A61B 8/085* (2013.01); *A61B 8/463* (2013.01); *A61B 8/5223* (2013.01); *G06V 20/70* (2022.01)

(58) Field of Classification Search
　　CPC .... G06V 10/00; G06V 10/764; G06V 10/765; G06V 10/74; G06T 7/0012; G06T 7/0014; G06T 7/0016; A61B 8/5215; A61B 8/5223; A61B 8/5292
　　See application file for complete search history.

(56) References Cited

U.S. PATENT DOCUMENTS

| | | | |
|---|---|---|---|
| 2015/0173715 A1* | 6/2015 | Raghavan | .............. G16H 40/67 |
| | | | 600/443 |
| 2021/0137416 A1 | 5/2021 | Canfield | |
| 2021/0150693 A1 | 5/2021 | Fornwalt | |
| 2021/0177374 A1 | 6/2021 | Balicki | |
| 2021/0259664 A1 | 8/2021 | Hare, II | |
| 2022/0296219 A1* | 9/2022 | Aladahalli | .............. A61B 8/469 |
| 2022/0361799 A1 | 11/2022 | Hong | |

OTHER PUBLICATIONS

Echocardiogram definition (www.medlineplus.gov/ency/article/003869.htm; retrieved Apr. 27, 2023).

(Continued)

*Primary Examiner* — Carolyn A Pehlke

(57)　　　　ABSTRACT

For robust view classification and measurement estimation in sequential ultrasound imaging, the classification and/or measurements for a given image or sequence of images are gated. To prevent oscillation in results, the gating provides consistent output.

20 Claims, 3 Drawing Sheets

(56)           References Cited

OTHER PUBLICATIONS

Ostvik, A., Smistad, E., Aase, S. A., Haugen, B. O., & Lovstakken, L. (2019). Real-time Standard View Classification in Transthoracic Echocardiography using Convolutional Neural Networks. Ultrasound in medicine & biology, 374-384.

Wu, L., Cheng, J.-Z., Li, S., Lei, B., Wang, T., & Ni, D. (2017). FUIQA: Fetal Ultrasound Image Quality Assessment With Deep Convolutional Networks. IEEE Transactions on Cybernetics, 1336-1349.

Xu, Z., Huo, Y., Park, J., Landman, B., Milkowski, A., Grbic, S., & Zhou, S. (2018). Less is More: Simultaneous View Classification and Landmark Detection for Abdominal Ultrasound Images. MICCAI. Cham: Springer. pp. 1-8.

\* cited by examiner

| Image Patient with Ultrasound | ~10 |

| Classify Views | ~12 |

| Measure in Classified Views | ~14 |

| Limit Display to Consistent Class and Measure | ~16 |
| Filter/Gate Classification | ~17 |
| Filter/Gate Measurement | ~18 |

FIG 4
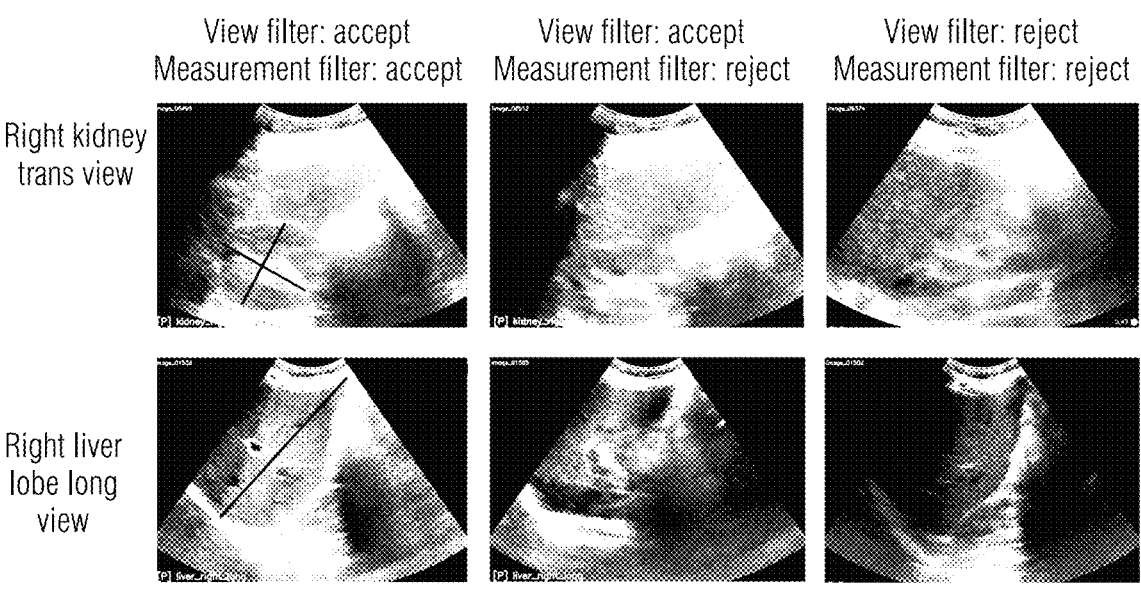
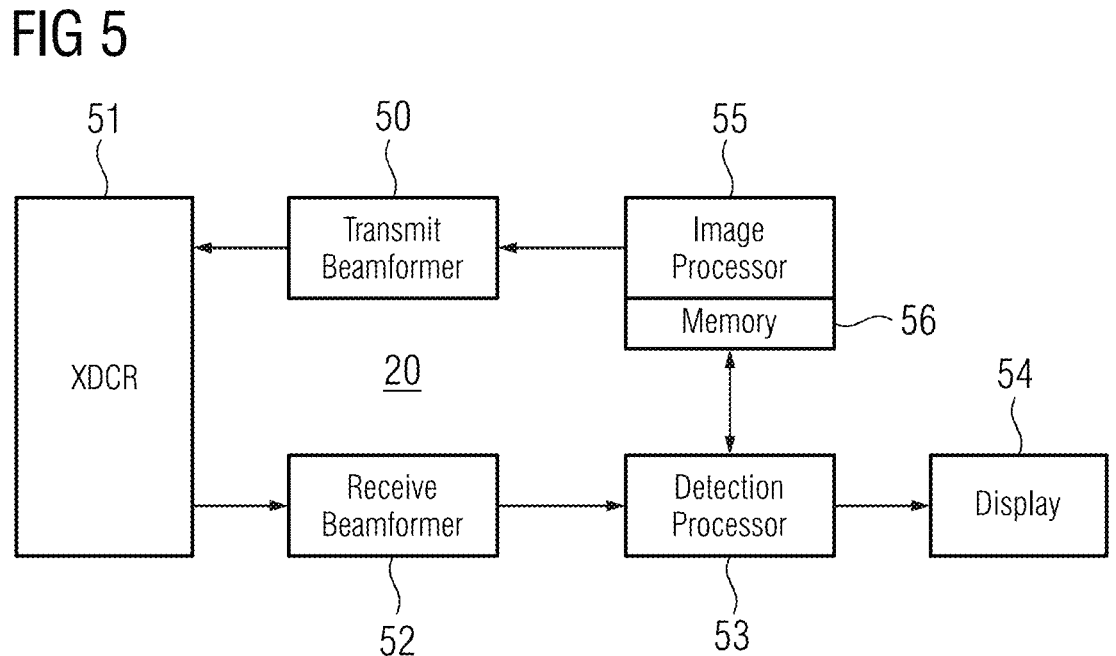
FIG 5

ROBUST VIEW CLASSIFICATION AND MEASUREMENT IN ULTRASOUND IMAGING

PRIORITY

This application claims priority to and is a continuation of U.S. patent application Ser. No. 17/325,257, filed May 20, 2021, which is incorporated by reference herein in its entirety.

BACKGROUND

The present embodiments relate to ultrasound imaging. In abdominal ultrasound examinations, several minutes of real-time imaging at about 20 frames per second is performed, which results in thousands of individual frames to cover all relevant views. The sonographer typically follows a medical guideline to examine organs or other anatomical structures of interest, thereby generating a continuous stream of sequential imaging data.

During the scan, the sonographer manually selects "key images," which are then stored with an identified view label (e.g., "left kidney transversal", "common bile duct", . . . ). For some of these key images, the sonographer further measures certain quantities of interest (e.g., kidney length, width, and/or height, lumen diameter, gallbladder wall thickness, . . . ). Measurement is typically done after the user found a proper view (e.g., high image quality, organ coverage, . . . ), then "freezes" the image, and finally places measurement calipers on the image. Key image selection, view identification, image "freezing", and measurement caliper placement are done manually on-the-fly while scanning. These manual steps are prone to user error and may be inconsistent across sonographers (e.g., typos, different abbreviations, inter-user variability). The quality of the results depends on user experience and skill. Given the number of images, the overall process can be inefficient and tedious.

Image processing, such as based on artificial intelligence, attempts to automate some of these manual tasks. An individual image is input to perform one or more of these tasks on that image. This approach may lead to unstable predictions image-by-image. The user typically selects the key image to input, and there is no guarantee that the one frame the user selected gives the optimal result by the artificial intelligence.

SUMMARY

By way of introduction, the preferred embodiments described below include methods, computer readable storage media, instructions, and systems for robust view classification and measurement estimation in sequential ultrasound imaging. The classification and/or measurements for a given image or sequence of images are filtered and/or gated. To prevent oscillation in results, the filtering and/or gating provides consistent output.

In a first aspect, a method is provided for sequential imaging with an ultrasound scanner. A patient is scanned with the ultrasound scanner. The scanning results in a sequence of frames of ultrasound data representing the patient. A view is classified for at least some of the frames of ultrasound data of the sequence. The classified views from multiple of the frames of ultrasound data are gated, where the gating of the classified views rejects a first one of the classified views and passes a second one of the classified views. Structure in the frames of ultrasound data are automatically measured. The frames where measurement is performed are the frames that pass the gating of the classified views. Results of the measuring from the frames that pass the gating of the classified views are gated. The gating of the results of the measuring rejects a first one of the results of the measuring and passes a second one of the results of the measuring. Images of the frames of data are displayed. The images include annotation for the classified views passed by the gating of the classified views. The images include the results of the measuring passed by the gating of the results of the measuring. The display is free of classified views from any of the frames of ultrasound data rejected by the gating of the classified views and free of the results of the measures rejected by the gating of the results of the measuring.

In a second aspect, a method is provided for view classification and measurement in ultrasound imaging by an ultrasound scanner. The ultrasound scanner images a patient as part of an abdominal examination. The imaging generates images of an abdomen of the patient. Structure represented in the images is classified. The structure is measured. Only the images with consistent classification of the structure and consistent measurement of the structure are displayed.

In a third aspect, a system is provided for stable classification and measurement in ultrasound imaging. An ultrasound imager is configured to scan with ultrasound. A processor is configured to classify views from the scan, measure structure in the views, and determine which of the classifications and measurements to display. A display is configured to display first images for the classifications and measurements determined by the processor to display and not display the classification and measurements determined by the processor to not display.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 4 shows example images; and

FIG. 5 is one embodiment of an ultrasound system for view classification and measurement.

DETAILED DESCRIPTION OF THE DRAWINGS AND PRESENTLY PREFERRED EMBODIMENTS

During ultrasound imaging, hundreds or thousands of images may be generated in a given examination of the patient. If, for example, an ultrasound system automatically and in real-time with the scanning classifies the view for each image and presents the predicted view label immediately to the user, then even a small fraction of misclassifications can be distracting. The user might lose trust in the system. Similarly, variation due to occasional errors in displayed measurement results may cause trust issues.

An automatic, customizable temporal filtering pipeline may be used to reduce or avoid inconsistency in the classification and/or measurements during ultrasound examination. The approach is executed in real-time in an ultrasound system with real-time capable view classification and measurements algorithms. One or more filtering modules limit or gate the output. In real-time (or retrospectively on archived data), the view classification and measurement results are provided from a stream of temporal image data. The view classification and measurement results of a given view classification most likely of sufficient quality are shown to the user. The display of wrong or inaccurate view label or measurement results is suppressed. Wrong or inaccurate results may be replaced with the correct, estimated, or improved results.

Image-level predictions are combined with temporal information to provide a better user experience for sonographers. Bad results that may have been produced are filtered out before the user sees them. "Flickering" (e.g., frequent change of view labels in case a classifier cannot properly differentiate one organ from another) is avoided by exploiting temporal and/or other information. Better performance increases the measurement accuracy by combining information from multiple frames or information about a frame. Mislabeling of individual frames is reduced by combining information from multiple frames. Some filtering modules enable exploitation of temporal information even if the employed view or measure algorithms do not support multi-frame input. Given the same input sequence, the filter pipeline produces identical output, avoiding sonographer-based variation. Manually selecting a key view can be replaced by filtered view classification results. Manually "freezing" a frame may be replaced by combination of multiple filtering modules (e.g. view classification filters+ measurement-filters (image quality, stability, . . . )). Manual caliper placement may be avoided.

Figures 1, 2:
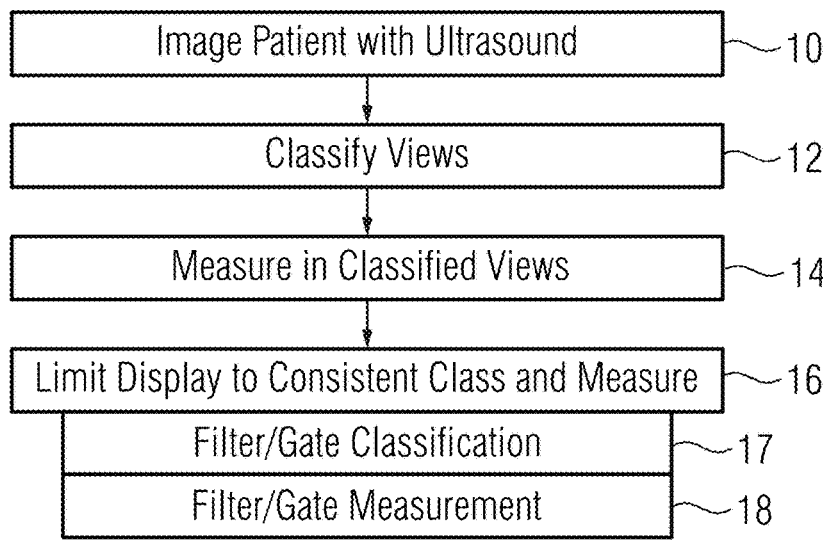
FIG. 1 is a flow chart diagram of one embodiment of a method for view classification and measurement in ultrasound imaging by an ultrasound scanner.
FIG. 2 illustrates an example arrangement for view classification and measurement in ultrasound imaging by an ultrasound scanner.

FIG. 1 is a flow chart diagram of one embodiment of a method for sequential imaging with an ultrasound scanner. The method provides for view classification and measurement in ultrasound imaging by the ultrasound scanner. Results of classification and/or measurement are gated. Variance in the results is reduced by gating, providing a better user experience in automated classification and measurement while hundreds or thousands of images are generated.

The method is implemented by the system of FIG. 5 or a different system. For example, an ultrasound scanner generates ultrasound images using beamformers and a transducer. An image processor automatically classifies views represented in the images and measures structures in the classified views. The image processor, using a display, limits the display to consistent classification and measurement.

Additional, different, or fewer acts may be provided. For example, the method is performed without imaging in act 10, such as performing the other acts on a stored imaging sequence. As another example, the method is performed without gating classification in act 17 or without gating measurements in act 18. The acts are performed in the order described or shown (e.g., top to bottom), but may be performed in other orders.

In act 10, the ultrasound scanner images a patient. The imaging is part of an abdominal examination, such as scanning the gall bladder, kidney, and/or liver of the patient. The imaging generates images of an abdomen of the patient. In alternative embodiments, the ultrasound imaging is of other parts of the patient, such as the heart.

The scanning results in a sequence of frames of ultrasound data representing the patient. Each frame of ultrasound data represents a region or field of view of the transducer for a given time or scan period. Any rate of imaging may be provided, such as ten, twenty, or more frames per second. The examination or continuous scanning occurs over any period, such as tens of seconds or minutes. There may be hundreds or thousands of images generated during a given abdominal examination of a patient.

Each frame is of ultrasound data to be processed for display as an image or ultrasound data formatted for display on a screen. The images may be data to be used to generate an image, data formatted for display, or data that was displayed. The frames of ultrasound data and/or images are from any point in the ultrasound image processing pipeline, such as after beamformation through viewing on a display.

The ultrasound scanner generates ultrasound images of the patient. The images are generated by scanning the patient. Alternatively, the images are generated by loading frames of data from a memory. The images were generated from a previous scan of the patient stored in memory.

Any type of ultrasound images may be generated, such as B-mode, flow mode (e.g., Doppler velocity or power), contrast agent, harmonic, pulsed wave Doppler (i.e., spectral Doppler), M-mode, Doppler tissue (i.e., tissue motion), or other ultrasound imaging mode representing acoustic interaction with the patient. The different modes detect different types of information, such as intensity of acoustic return (e.g., B-mode and M-mode) or velocity (e.g., flow mode or Doppler tissue).

To acquire the images, the ultrasound transducer may be moved along the patient. The movement is along a skin of the patient but may be along a vessel or organ within the patient (e.g., scanning with a probe or catheter). Rotation of the transducer may be used. The overall process for scanning and imaging includes placing the transducer on the patient, rotating and/or translating the transducer to image the patient, scanning while the transducer moves, and generating images.

During the ultrasound imaging, a large amount of data is collected. Each scan of a plane or volume provides a frame of data. An image may be generated from each frame. Tens, hundreds, or thousands of frames and/or images are created for examining the patient in one examination (e.g., one implementation of the predetermined pattern and/or during a given visit of a patient to the sonographer).

Rather than using manual identification of key images and manual placement of calipers or other markers for measurement, the classification and measurement are automated. Acts 12 and 14 represent the automation of the classification and measurement, respectively. To avoid distracting or distrust building rapid variation in the classification or measurement through the sequence, the display of inconsistent outputs of class or measurements is limited in act 16. In some cases, the limitation is more than low pass filtering the output, allowing for more confidence in the output results.

FIG. 2 shows a schematic representation of an example sequential pipeline that filters both view classification results (i.e., decides when to show view labels) and measurements (i.e., decides when to display measurements). The ultrasound scanner 20 generates a sequence of images 21 in a real-time image stream (e.g., at about 20 frames per second), resulting in a plurality of images 22. Each image is classified in act 12 by the view classification algorithm 23. The results from the classification (i.e., view label) are passed to one or more (up to $N_{view}$) filter modules 24, which apply gates 25 to pass or reject the view label. The view labels that pass the filters 24 and gates 25 are displayed 29A. The measurement algorithm 28 is applied to images 22 associated with passed view labels. The results from the measurement (e.g., distance values) are passed to one or more (up to $N_{meas}$) filter modules 26, which apply gates 27 to pass or reject the measurement. The measurement values that pass the filters 26 and gates 27 are displayed 29B.

Which view classification and measurement results of a given view classification and measurement algorithm are most likely of sufficient quality to show to the user are determined in real-time (or retrospectively on archived data) from the stream 21 of temporal image data. The display of wrong or inaccurate results is rejected or replaced with the correct or improved results by combining image-level predictions with temporal information.

FIG. 2 shows $N_{view}$ and $N_{meas}$ filters 24, 26 and gates 25, 27. Any value of $N_{view}$ and $N_{meas}$ may be used, such as 1-3. FIG. 2 shows a sequential pipeline (logical AND). In other embodiments, other arrangements may be used. For example, filtering modules 24, 26 may be organized in parallel streams (logical OR) or other arrangements. The display 29A of the view label may be conditioned on the corresponding measurement also being passed by the gates 27. The view filtering may operate in parallel, the measure filtering may operate in parallel, and/or the view filtering may be in parallel with the measurement filtering. Furthermore, feedback loops or other more complex architectures may be implemented to further improve the robustness and accuracy of view classifier and measurement results.

Referring again to FIG. 1, the image processor, implementing the view classification algorithm 23, classifies a view for each of the frames of ultrasound data of the sequence. The classification labels the content of the view, such as indicating that the image shows a particular organ or anatomical structure. The structure represented in the images are classified automatically.

The ultrasound scanner or an image processor applies computer-assisted detection to each of the frames or images of the sequence acquired by the scanning. Any now known or later developed computer-assisted detection may be applied. For example, pattern matching is used to determine whether a pattern indicative of a particular view is located in the frame or image. As another example, thresholding, segmentation, or other image processing is applied. For more rapid detection, a machine-learned detector may be applied. The machine-learned detection is a Bayesian network, support vector machine, neural network, or another detector relating input (e.g., the image 22 or features from the image 22 (e.g., steerable features or Haar wavelets)) to output classification. The view classification algorithm 23 is not fixed. The view classification may be replaced with other algorithms. Alternatively, multiple algorithms 23 per task could be used and each filtering module could decide which results to use.

Different computer-assisted classifiers may detect different types of objects and/or objects in different situations. Multiple classifiers may be applied to each frame. In one embodiment, the classifiers to be applied are selected based on the type of examination. For example, the user configures the ultrasound scanner for a liver examination. A classifier or classifiers for detecting the liver view and/or suspicious objects (e.g., tumors and/or cysts) in the liver are selected and applied. As another example, the user configures the ultrasound scanner for kidney examination. A classifier or classifiers for labeling kidney views with or without programming to label views for adjacent organs are selected. The selection is automatic by the processor, or the user selects the classifiers.

The classification may be binary, such as classifying where a given view is shown or not. A hierarchy of binary classifiers may be provided for identifying the class or view from among any number of different views. Alternatively, the classifier identifies between two or more different views.

The computer-assisted classification is applied to all of the frames. In other embodiments, the detection is applied to fewer than all the frames. The computer-assisted classification is applied during the acquisition of the frames or images. The application is in real-time. The period to process a frame is equal to or less than the period to acquire a new frame, allowing the application to occur in real-time, such as completing application of the detection within a 20-100 milliseconds (e.g., 50 ms) of creating the scan. In other embodiments, the application occurs in a post process after scanning is complete. Combinations of application of detection during the scanning and as a post process may be used.

In act 14, the image processor automatically measures from the frames of ultrasound data. The frames on which the measurement is performed may be only the frames with a view passing the limitation of act 17, all frames, or another sub-set of frames.

Any measurement may be performed. For example, a distance (e.g., liver height or wall thickness), area, or volume is measured. Other measurements, such as curvature, surface characteristic, angle, range of motion, or compression, may be measured.

The measurement is performed by detecting one or more landmarks or other structures to define the measurement (e.g., identify two landmarks to place calipers for measuring distance between the landmarks). Any now known or later developed computer-assisted detection may be applied. For example, pattern matching is used to locate one or more landmarks. As another example, thresholding, segmentation, or other image processing is applied. In another example, a statistical shape model or abdomen model is fit to the frame of data. For more rapid detection, a machine-learned detector may be applied. The machine-learned detection is a Bayesian network, support vector machine, neural network, or another detector relating input (e.g., the image 22 or features from the image 22 (e.g., steerable features or Haar wavelets)) to output landmark location or directly to the measurement. The measurement algorithm 28 is not fixed. The measurement algorithm may be replaced with other algorithms. Alternatively, multiple algorithms 28 per task could be used and each filtering module 26 could decide which results to use.

Different computer-assisted measurement algorithms may perform different measurements, such as one for measuring height and another for width. Multiple measurement algorithms may be applied to each frame. Different measurement algorithms may be used for different types of objects and/or objects in different situations. Separate gating or dependent gating may be used for the different measurements.

In one embodiment, the measurement algorithm(s) to be applied are selected based on the type of examination. The selection is automatic by the processor, or the user selects the classifiers.

In act 16, the image processor causes the display images from the frames of data of the sequence. The image processor limits the display of the view labels from the classification and/or the measurements without limiting the images. Any image with an unreliable view label or measurement is shown without the label or measurement, or a replacement label or measurement is presented. Alternatively, the image processor causes the display to display only the images with consistent classification of the structure and/or consistent measurement of the structure.

To limit the display of labels and/or measurements, the image processor temporally filters the classifying and temporally filters of the measuring. The view labels, measurements, and/or images where the classification and the measurement are different within a temporal window are rejected and not displayed. The filtering acts to gate the classifying and the measuring such that display of any deviating structure and any deviating measurement is suppressed. Act 17 is for filtering and gating of the classification (classification results), and act 18 is for filtering and gating of the measurement (measurement results). Any filtering and/or gating arrangement (see FIG. 2) may be used.

Various types of filtering and corresponding gating may be provided. For example, the classification is gated in act 17 with temporal filtering, sequence-level classification, and/or dynamic system modeling. As another example, the measurement is gated in act 18 with image quality, motion detection, measurement stability, measurement aggregation, sequence-level measurement, and/or spatial-temporal tracking.

In act 17, the image processor gates the classified views from multiple of the frames of ultrasound data. The gating of the classified views rejects some of the classified views and passes others of the classified views. Where the classification is the same for all the frames in a window, then all the view labels are passed. Where all the view labels are different, then none of the view labels pass. Layered gating may be used, such as applying two different gating criteria and/or filtering differently as part of the gating. Any labels passing the multiple criteria are displayed. Any labels failing one of the multiple criteria are not displayed.

The window is temporal, such as gating based on the labels of the last M frames. A first-in-first-out (FIFO) buffer, memory, or another queue is used to define the window. The gating is based on the classified views and/or frames of the classified views in the FIFO queue. If the view change is consistent, then the view label output will change. Until the view change is consistent, then the current view label is used. In additional or alternative embodiments, the window defines a spatial or other filtering. Different regions represented in the frame are classified separately, and/or different filtering is applied to a given image and the classification is applied separately to the filtering results.

Various different filtering modules and corresponding gating may be provided. Any of the modules may be used alone (e.g., $N_{view}=1$) or may be one module in a pipeline or arrangement of multiple modules (see FIG. 2). Other embodiments than described below may use other filtering and gating.

In one embodiment, a temporal filtering approach is used for gating the view labels. The classified view where a threshold number or percentage of the classified views in a window of classified views are a same classified view are passed, and any different classified views in the window are rejected. For example, each $Image_t$ (at timestep t; e.g. current frame in real-time image stream) is input. The view classification algorithm is run on each $Image_t$, resulting in view label $v_t$. The view label $v_t$ is stored in the FIFO memory queue with capacity n. If the FIFO memory is at capacity (n) and at least m (m≤n) of the stored labels are identical (e.g. all of them are "spleen long"), then the gate is opened, and $v_t$ (e.g., "spleen long") is output. Otherwise, $v_t$ for the most recent or current image t is rejected (i.e., do not open the gate). Another pass or gate criterion may be used. For example, the gate is opened, and v* is output where v* is, for example, a majority vote of all $v_t$-$v_{t-n}$ in the FIFO memory. In this temporal filtering, if the last frames gave consistent view classification results, it is more likely that the current view label is correct.

Figure 3:
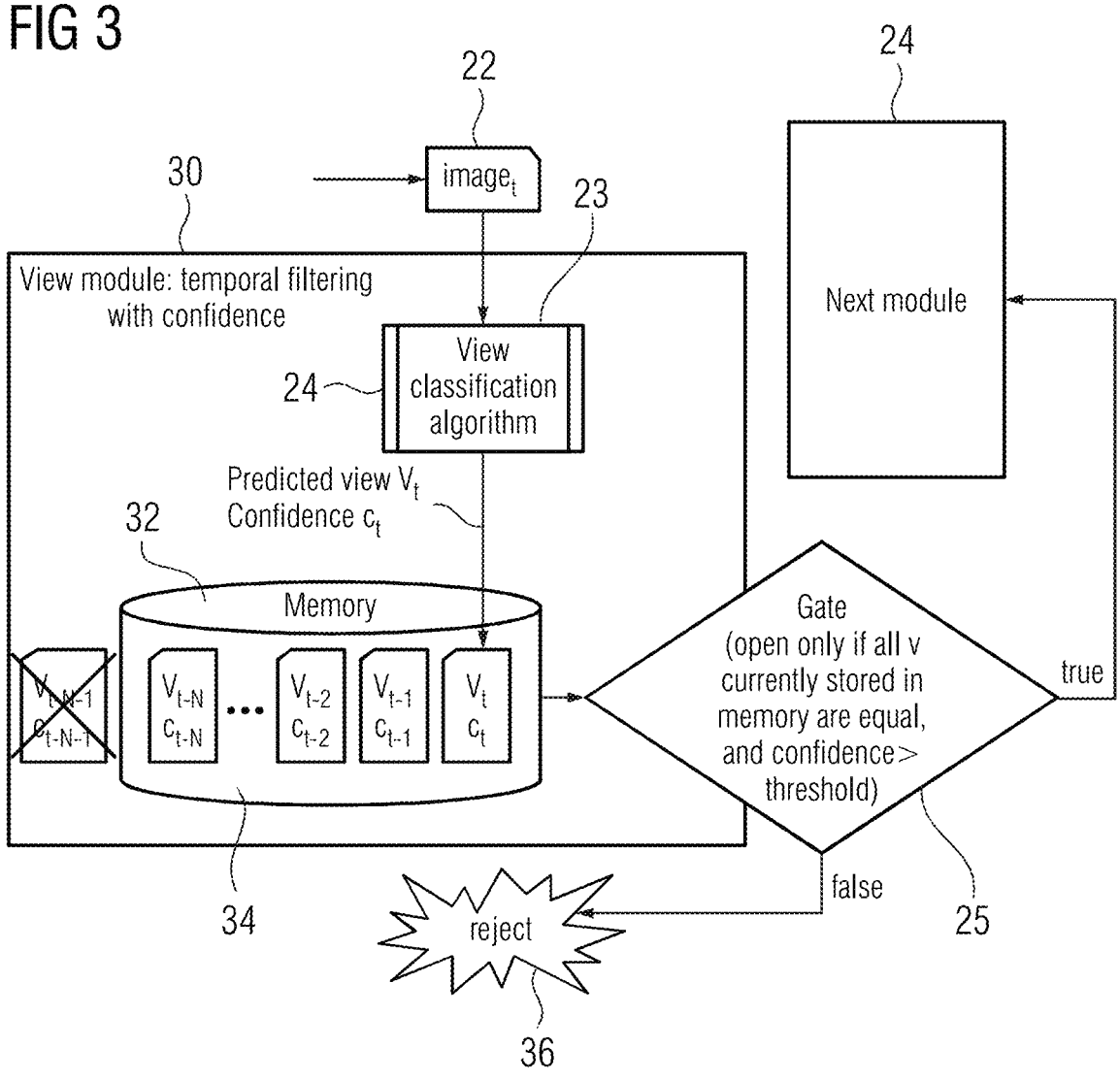
FIG. 3 illustrates an example temporal filtering of classification results with confidence for gating.

In another embodiment, the temporal filtering includes confidence information. The image processor determines a confidence for each of the classified views. The gating relies, at least in part, on the confidence. Only the view labels where the threshold number or percentage of the classified views in the window are the same classified view and have a confidence above a confidence threshold are passed. For example and as shown in FIG. 3, the image (at timestep t; e.g. current frame in real-time image stream) 22 is input to the view classification algorithm 23. The view classification algorithm outputs the view label $v_t$ as well as a confidence $c_t$. A machine-learned network may be trained to classify and also output a confidence in the classification. Other sources of confidence may be used, such as a degree of correlation of the image with a template or fuzzy logic-based confidence.

The view label $v_t$ and the confidence $c_t$ are stored in the FIFO memory 32 or queue with the capacity n. If the FIFO memory is at capacity (n) and at least m (m≤n) of the stored labels are identical and the confidence measure is above user-defined threshold (e.g. accumulated confidence for all n in Memory, or a subset, or only the last frame), then the gate 25 is opened and $v_t$ is output, such as to the next module 24 or to the display. If the confidence is low or the view label does not match the majority or threshold number in the memory 32, then the view label $v_t$ for the current frame is rejected 36. A replacement is used, or no label is output. In another approach, v* is output where v* is a confidence-weighted majority vote of all $v_t \ldots v_{t-n}$ the FIFO memory. If the last frames gave consistent view classification results and the classifier was also confident in the predictions, it is very likely that the current view label is correct.

In yet another embodiment, the image processor applies a sequence-level classification for gating. The classification of act 12 uses a concatenation of multiple frames as the input. The n frames are concatenated, such as grouped in the FIFO memory. As new frames are added and oldest frames are removed, different temporal windows are provided for the concatenation. The classification is then performed based on the concatenated group of frames for a given window. The gating is then based on the classified view label for the concatenation. This is similar to temporal filtering but where the classification algorithm directly decides results for multiple images instead of imposing a voting scheme on top of a single-image classifier. A classifier algorithm that supports multi-image input, such as a classifier machine trained on image sequences instead of individual images, is applied. Confidence may be used in the gating criteria as well, such as requiring a threshold confidence in the classification from the concatenation.

In an example, $image_t$ is input. The $image_t$ is stored in the FIFO memory with capacity n. If the memory is at capacity, all n images currently in memory are combined (e.g. concatenated). The view classification algorithm is run on the combined image. The gating is always pass where a given view of a given frame may be different than the collection or combination of frames since the classification is based on the collection or combination. Confidence may be used to reject any view labels such as where variation in possible views in the combination of frames is high.

In another embodiment, the image processor gates as a dynamic system with state change. Temporal view classification is formulated as dynamic system with states, state-to-state transition probabilities, and observations. The state is the most likely current view (e.g. "kidney left trans" or "gallbladder long", . . . ), such as output by the classification algorithm. The transition probabilities are prior probabilities of going from one state x to another state y. The transition probabilities may be machine learned from annotated training data sequences, defined manually by experts, or based on clinical guidelines for abdominal ultrasound exams. The observation is the output of the view label or classification for a given image. The dynamic system decides, based on current state, temporal state trajectory, current (and previous) observations, and transition probabilities, what is the next state (e.g. stay at current state, or transition to different state). A confidence in the state may be used in the decision to determine the observation. Using the state is passing by the gate. Where the observation is different than the state, then the state is rejected, and a replacement used.

Incorporating prior knowledge may be useful to improve results. It can help to remove "impossible" state transitions and favor likely state transitions (e.g. within a continuous image sequence, going from liver to gallbladder within few frames is very likely due to high proximity of both organs; whereas going from left kidney to right kidney in very short time is very unlikely; such "jumps" can be detected and filtered with this approach). The dynamic system may be implemented as a Hidden Markov Model, a Recurrent Neural Network, a Long-term-short-term memory neural network, or another approach.

In act 18, the image processor gates results of the measuring from the frames that pass the gating of the classified views or from other frames (e.g., input of frames independently of passing the classified view gating). Gating of the results of the measuring rejects some results of the measuring and passes other results of the measuring. Where the measurements are consistent, then all of the measuring results may be passed. Where the measurements are all different outside of a tolerance, then all of the measuring results may be rejected, at least in a given window.

Layered gating may be used, such as applying two different gating criteria and/or filtering differently as part of the gating. Any measurement results passing the multiple criteria are displayed, and any measurement results failing to pass one of the criteria are rejected.

The window for gating the measurement results is temporal, such as gating based on the labels of the last M frames. A first-in-first-out (FIFO) buffer, memory, or another queue is used to define the window. The gating is based on the measurement results and/or frames of the measurement results in the FIFO queue. If a change in the measurement results is consistent, then the output measurement result will change. Until the change is consistent, then the current measurement result is used. In additional or alternative embodiments, the window defines a spatial grouping or different filtering. Different regions represented in the frame are measured separately, and/or different filtering is applied to a given image and the measurement is applied separately to the filtering results. In other embodiments, the gating is applied based on the input image without temporal or other windowing.

Various different filtering modules and corresponding gating may be provided. Any of the modules may be used alone (e.g., $N_{meas}$=1) or may be one module in a pipeline or arrangement of multiple modules (see FIG. 2). Other embodiments than described below may use other filtering and gating.

In one embodiment, the image processor gates each frame based on quality of the frame of ultrasound data. Low-quality images are rejected, and good quality (above a threshold level) are passed. Any quality metric may be used, such as level or variance in contrast or gradients, or intensity histogram features. Machine-learned quality metrics may be used (e.g., input an image to the machine-learned model, which outputs the quality level).

In another embodiment, the image processor gates measurement or measurement results based on an amount of motion. The temporal difference or motion in the window is used. Multiple sequential images are stored, such as in a FIFO queue. A new image is compared to the previous image(s) to determine motion. Motion may be determined by any of various metrics, such as sum of absolute difference, squared differences, pixel-wise intensity difference between images, or more sophisticated motion detectors (e.g. based on local feature detectors, or others). Where motion is above a threshold, the measurement algorithm is not applied, or the results are rejected. Where the motion is below the threshold, then the measurement algorithm applied and/or the measurement result for that frame is passed. If the difference between subsequent frames is high, this may indicate motion (either motion of transducer or organ movement, . . . ) and the individual image quality is likely low (blurred borders, other motion artifacts). The low quality may not be suitable for accurate measurement computation, such as quality resulting in inaccurate landmark detection.

In yet another embodiment, the image processor gates measurement results based on measurement stability of the results. Temporal measurement stability is used as the criterion of the gating. The measurement algorithm is run, and the measurement results (e.g. landmark locations or distance between landmark locations) over n frames (time window) are stored. The gate is opened and the measurements output to user only if the variability between the measurements in the analyzed time window is below a certain threshold. For measuring structures, sonographers typically try to scan the structure of interest over multiple frames or seconds until reaching a stable image with good quality. The stability gating emulates this user approach.

In a further embodiment, the temporal measurement stability gating includes confidence. The confidence of the measurement algorithm in the measurement results is output and used with the stability to gate. The measurement algorithm may output confidence, such as a machine-learned model trained to output the measurement value or landmark locations and confidence. In an alternative approach, the filter module computes confidence based on the measurements (e.g. by evaluating a shape model or other metric). The gate passes only stable and confident measurement results and rejects instable or low confidence measurements.

In another embodiment, the image processor gates the measurement results by aggregation or smoothing. The stability may be used as an additional criterion so that the aggregation is only of stable measurement results or images. For example, the measurement results and images of last n frames are stored. The stability is checked for the n frames, such as using a correlation or difference. Where the difference is low or correlation high, then the imaging is stable within the window. If stable, the measurement results are aggregated, such as computing a mean or median for each landmark or landmark configuration or for the measurement values (e.g., distances). The aggregated results are output along with the image corresponding (or closest to) to that result. The aggregated results might not perfectly match the latest image, such as where an "older" image (within time window) is output, rejecting the current frame.

In yet another embodiment, the image processor applies an image sequence-based measurement prediction for gating. The measurement is estimated from a concatenation of the frames, such as frames passing the gating of the classified views. The gating of the measurement is based on the concatenation. The measurement algorithm operates on multiple sequential images as input to compute a measurement result instead of just a single image-based computation.

In a further embodiment, the image processor gates with spatial-temporal tracking. For measurement algorithms that take as input a single image to compute the output measurements (e.g., distance) and/or landmark locations, a combination of temporal and spatial tracking is used. The measurement algorithm outputs a single-image landmark output. This is performed for each frame in the temporal window. A temporal object tracking algorithm is applied to track the landmark(s) between frames, providing two sources of the position of the same landmark. The similarity in location may be used to indicate confidence or stability. A threshold position difference may be used to gate. Where the landmark locations are similar, then the gate passes the landmarks (e.g., averaged locations) for use in determining the value of a measurement (e.g., distance).

In act 16, the image processor causes display of images of the frames of data passed by the gating of the classified views. The display is free of images from any of the frames of ultrasound data rejected by the gating of the classified views. All images whether passed or not may be displayed but only classification view labels passed by the gating are displayed with the images. The annotations showing the view label to the user are restricted to be the passing labels and not the labels that did not pass.

The displayed images may include the results of the measuring passed by the gating of the results of the measuring. Only landmarks or values of measurement passed by the gating are displayed on the image. The images are free of the results of the measuring rejected by the gating of the results of the measuring. In other embodiments, the only view labels, measurement results (landmarks and/or values), and/or images displayed are for a frame where both the view label and measurement results pass the gating.

FIG. 4 shows some example images with corresponding gating results. The images are examples from a sequence of other 8,000 sequential images in a full abdominal examination. The classification view filtering used temporal filtering with confidence for gating the classification views and temporal measurement stability with confidence for gating the measurement results. A deep learning (DL)-based single-image view classification is used, and a DL-based single image measurement algorithm is used to measure distance. The classifications in the example of FIG. 4 are for right kidney trans view and right liver lobe long view.

Images that were accepted by all modules of the filtering pipeline, shown in the left column, are good quality images where the organ of interest can be identified with high certainty and the measurement can be computed with high certainty. The view label may be an annotation in the bottom left corner of image or another location. The measurement may be an annotation for the value and a line as a graphic on the image showing the location of the measurement (i.e., showing the calipers).

Images in the middle column were accepted by the view classifier and correctly labeled, but measurements were automatically filtered or rejected, most likely due to blurry quality and henceforth low measurement classifier confidence. The right column shows images that were fully rejected by the pipeline. The view classifier confidence did not score high enough, hence no view label was shown to user. Low confidence was most likely due to low quality images with organs partially out of the field of view.

FIG. 5 shows one embodiment of an ultrasound system 20 for stable classification and measurement in ultrasound imaging. For imaging an abdominal region or other region of the patient, a sequence of images is generated. The view is automatically labeled and measurements automatically performed for the images of the sequence. Using gating, the annotations for the views and measurements are made more consistent than would be the case without gating. Only view labels and/or measurements that are consistent are displayed. Only images with consistent views and/or measurements may be displayed. Alternatively, images are displayed but the annotations for view or measurement are gated.

The ultrasound system 20 is a medical diagnostic ultrasound imaging system. In alternative embodiments, the system 20 is a personal computer, workstation, PACS station, or other arrangement at a same location or distributed over a network for real-time or post acquisition imaging through connection with beamformers 50, 52 and transducer 51.

The system 20 implements the method of FIG. 1, the approach of FIG. 2, or other methods. The system 20 includes a transmit beamformer 50, a transducer 51, a receive beamformer 52, an detection processor 53, a display 54, a memory 56, and a processor 55. Additional, different or fewer components may be provided. For example, a user input is provided for manual or assisted designation of thresholds, selection of type of gating, and/or for configuring the ultrasound system 20 for imaging.

The transmit beamformer 50 is configured to generate waveforms for a plurality of channels. The waveforms are generated and applied to a transducer 51 with any timing or pulse repetition frequency. Upon transmission of acoustic waves from the transducer 51 in response to the generated waves, one or more beams are formed during a given transmit event. The beams are for B-mode, color flow mode, elasticity, shear wave, and/or other modes of imaging. A sequence of transmit beams are generated to scan a one, two or three-dimensional region. Sector, Vector®, linear, or other scan formats may be used. Multiple complete scans are performed to generate a corresponding multiple frames of ultrasound data.

The transducer 51 is a 1-, 1.25-, 1.5-, 1.75- or 2-dimensional array of piezoelectric or capacitive membrane elements. The transducer 51 includes a plurality of elements for transducing between acoustic and electrical energies. For example, the transducer 51 is a one-dimensional PZT array with about 64-256 elements.

Receive signals are generated in response to ultrasound energy (echoes) impinging on the elements of the transducer 51. The receive beamformer 52 includes a plurality of channels to apply relative delays, phases, and/or apodization to form one or more receive beams in response to each transmission for imaging. Dynamic focusing on receive may be provided. The receive beamformer 52 outputs data representing spatial locations using the received acoustic signals. Data for a single location, locations along a line, locations for an area, or locations for a volume are output. The data beamformed in response to a complete scan of a region is a frame of data.

The detection processor 53 is a B-mode detector, Doppler detector, pulsed wave Doppler detector, correlation processor, Fourier transform processor, filter, other now known or later developed processor for implementing an imaging mode, or combinations thereof. The detection processor 53 provides detection for the imaging modes, such as including a Doppler detector (e.g., estimator) and a B-mode detector. The detection processor 53 operates on and/or generates frames of ultrasound data. A spatial filter, temporal filter, and/or scan converter may be included in or implemented by the detection processor 53. The detection processor 53 outputs display values as frames of data, such as detecting, mapping the detected values to display values, and formatting the display values or detected values into a display format.

The image processor 55 is a control processor, general processor, digital signal processor, graphics processing unit, application specific integrated circuit, field programmable gate array, network, server, group of processors, data path, combinations thereof, or other now known or later developed device for classifying and/or measuring from ultrasound images. The image processor 55 is separate from or part of the detection processor 53. As a separate device, the image processor 55 requests, receives, accesses, or loads frames of data at any stage of processing (e.g., beamformed, detected, scan converted, display mapped or other stage) for classifying and measuring. The image processor 55 is configured by software, firmware, and/or hardware to perform or cause performance of acts 12-18 of FIG. 1.

The processor 55 is configured to classify views from the scan, measure structure in the views, and determine which of the classifications and measurements to display. The processor is configured to determine which of the classification and measurements to display based on a level of consistency through a sequence of the scan or other information that leads to more consistent output by gating.

The display 54 is a CRT, LCD, monitor, plasma, projector, printer, or other device for displaying an image or sequence of images. Any now known or later developed display 54 may be used. The display 54 is configured by loading an image into a display plane memory to display an image or a sequence of images. The display 54 displays two-dimensional images or three-dimensional representations.

The display 54 is configured to display one or more images with annotations for the classifications and/or measurements determined by the processor. The display 54 is configured to not display images and/or annotation for the classification and/or measurements where the gating rejects the classification and/or measurements.

The detection processor 53 and image processor 55 operate pursuant to instructions stored in the memory 56 or another memory. The instructions configure the system for performance of the acts of FIG. 1. The instructions configure the detection processor 53 and/or the image processor 55 for operation by being loaded into a controller, by causing loading of a table of values (e.g., imaging sequence), and/or by being executed.

The memory 56 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

In one embodiment, the memory 56 stores the classification, measurement, images, and/or scan. For example, the memory 56 stores a previous scan. Instead of real-time or on-the-fly classification and measurement while the sonographer scans, a sequence of previously recorded images are analyzed. A small subset of "best images" covering the relevant organs and/or structures and measurements may be automatically selected using filtering provided by the classification and/or measurement analysis.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed is:

1. A method for sequential imaging with an ultrasound scanner, the method comprising:
scanning a patient with the ultrasound scanner, the scanning resulting in a sequence of frames of ultrasound data representing the patient;
classifying a view for at least some of the frames of ultrasound data of the sequence;
gating the classified views from multiple of the frames of ultrasound data, the gating of the classified views including:
rejecting a first one of the classified views where a first classification from the first one of the classified views implies a jump in location by the ultrasound scanner; and
passing a second one of the classified views where a second classification from the second one of the classified views implies a continuous transition by the ultrasound scanner;
automatically measuring from the frames of ultrasound data, including the second one of the classified views, that pass the gating of the classified views;
determining confidence levels for results of the measuring;
gating the results of the measuring based on the confidence levels; and
displaying images of the frames of data, the images including annotation of the classified views passed by the gating of the classified views, the images including the results of the measuring passed by the gating of the results of the measuring, the displaying being free of annotations from any of the frames of ultrasound data rejected by the gating of the classified views and being free of results of the measuring rejected by the gating of the results of the measuring.

2. The method of claim 1 wherein scanning comprises scanning the patient in an abdominal examination, wherein measuring comprises measuring a distance, area, or volume.

3. The method of claim 1 wherein gating the classified views further comprises passing the classified view where a threshold number or percentage of the classified views in a window of classified views are a same classified view and rejecting the different classified views in the window.

4. The method of claim 3 wherein gating the classified views further comprises determining a confidence for each of the classified views, and only passing the classified where the threshold number or percentage of the classified views in the window are the same classified view and have a confidence above a confidence threshold.

5. The method of claim 1 wherein classifying the view further comprises concatenating the multiple frames of ultrasound data in different windows and classifying the concatenations of the multiple frames from the different windows, and wherein gating the classified views comprises gating the classified views from the concatenations.

6. The method of claim 1 wherein gating the classified views further comprises gating as a dynamic system with state change.

7. The method of claim 1 wherein gating the classified views further comprises storing the classified views or the frames of ultrasound data in a first-in-first-out queue and gating based on the classified views or the frames in the first-in-first-out queue.

8. The method of claim 1 wherein gating the results comprises gating based on quality of the frames of ultrasound data, respectively.

9. The method of claim 1 wherein gating the results comprises gating based on an amount of motion.

10. The method of claim 1 wherein gating the results comprises gating based on measurement stability of the results.

11. The method of claim 10 wherein gating the results comprises aggregating the results when the measurement stability is above a stability threshold.

12. The method of claim 1 wherein measuring comprises measuring from a concatenation of the frames that pass the gating of the classified views, and wherein gating the results comprises gating based on the concatenation.

13. The method of claim 1 wherein gating the results comprises spatial-temporal tracking.

14. A method for view classification and measurement in ultrasound imaging by an ultrasound scanner, the method comprising:

imaging, by the ultrasound scanner, a patient as part of an abdominal examination, the imaging generating images of an abdomen of the patient;

classifying, by the ultrasound scanner, structure represented in the images;

measuring, by the ultrasound scanner, the structure; and displaying only the classification consistent with smooth translation of the ultrasound scanner and displaying only consistent measurement of the structure.

15. The method of claim 14, wherein displaying comprises gating the classifying and gating the measuring such that display of any deviating structure and any deviating measurement is suppressed.

16. The method of claim 15 wherein gating comprises gating the classification further with temporal filtering, sequence-level classification, or dynamic system modeling and gating the measurement with image quality, motion detection, measurement stability, measurement aggregation, sequence-level measurement, or spatial-temporal tracking.

17. A system for classification and measurement in ultrasound imaging, the system comprising:

an ultrasound imager configured to scan with ultrasound;

a processor configured to classify views from the scan, measure structure in the views, and determine which of the classifications and measurements to display, the determination of which classifications to display is based on whether the classifications are consistent with progression of the scan without jumping; and a display configured to:

display, based on instructions from the processor, first classifications that are consistent with progression of the scan without jumping and first measurements determined by the processor to display; and not display, based on instructions from the processor, second classifications that indicate a jump within the scan and second measurements determined by the processor to not display.

18. The system of claim 17, wherein the processor is configured to determine which of the measurements to display based on a level of consistency through a sequence of the scan.

19. The system of claim 17, further comprising a memory configured to store the scan, and wherein the processor is configured to classify, measure, and determine from the stored scan.

20. The system of claim 17, wherein the processor is further configured to determine which of the classifications and measurements to display by further performing spatial-temporal tracking.

* * * * *